United States Patent [19]

Ramsey et al.

[11] Patent Number: 5,630,372
[45] Date of Patent: May 20, 1997

[54] ON DEMAND USEFUL LIFE INDICATOR

[76] Inventors: Joseph W. Ramsey, 11 Great Meadow La., East Hanover, N.J. 07936; Peter L. Gill, 1 Kenley Way, Hackettstown, N.J. 07840

[21] Appl. No.: 506,334

[22] Filed: Jul. 25, 1995

[51] Int. Cl.$^6$ .................................................. G01D 21/00
[52] U.S. Cl. ................................. 116/206; 426/87
[58] Field of Search ........................... 116/206, 207, 116/216, 217; 374/102, 162, 106, 161; 426/87, 88; 436/902, 904, 905

[56] References Cited

U.S. PATENT DOCUMENTS

| | | | |
|---|---|---|---|
| 2,918,033 | 12/1959 | Snyder | 116/206 |
| 2,918,893 | 12/1959 | Norton | 116/206 |
| 3,018,611 | 1/1962 | Biritz | 116/206 |
| 3,243,303 | 3/1966 | Johnson | 116/207 |
| 3,952,746 | 4/1976 | Summers | 116/206 |
| 4,205,043 | 5/1980 | Esch et al. | 116/206 |
| 4,212,153 | 7/1980 | Kydonieus et al. | 116/207 |
| 4,248,597 | 2/1981 | McNeely | 116/206 |
| 4,550,150 | 10/1985 | Patel et al. | 116/207 |
| 4,812,053 | 3/1989 | Bhattacharjee | 116/206 |
| 5,482,000 | 1/1996 | Ward | 116/217 |

*Primary Examiner*—Thomas B. Will
*Assistant Examiner*—Andrew Hirshfeld
*Attorney, Agent, or Firm*—Patrick J. Pinto

[57] ABSTRACT

An improved on demand useful life indicator that may be attached to or placed in manufactured goods at a selected time. This indicator includes a base member; an indicating material layer, an adhesive layer, and a co-layered covering material. The indicating material layer is formulated to provide a visual indication when exposed to a selected component of an ambient fluid. The indicating material is applied to one side of the impermeable base member in a selected pattern. The adhesive layer is made of an impermeable material and applied in a selected pattern over the indicating material layer so that at least one selected portion of the indicating material is exposed to the ambient fluid. An inner layer of the co-layered cover member has a greater adhesion to the adhesive layer when an impermeable outer layer is removed. The inner layer is permeable to the ambient fluid. The useful life indicator remains in a selected state of dormancy until the outer layer of the co-layered cover member is removed. This useful life indicator may include a self-contained norm of visual indication.

10 Claims, 1 Drawing Sheet

5,630,372

ON DEMAND USEFUL LIFE INDICATOR

BACKGROUND OF THE INVENTION

1. Field of the Invention

With regard to the classification of art, this invention is believed to be found in the general class entitled SIGNALS AND INDICATORS and more particularly to those subclasses pertaining to those that are CHEMICALLY ACTIVATED.

2. Description of Related Art

Useful life indicators are known in the prior art. One example in the known prior art is U.S. Pat. No. , 4,812,053 which issued to Bhattacharjee on Mar. 14, 1989. This cited patent has advanced the art but accuracy, repeatability and reliability still remain an identified need. The present invention addresses those above identified needs. The present invention provides a structure that allow at least one of its indicating portions to remain dormant from the time of manufacture until the time of activation. After activation, the present invention provides an indication means that is activated by a component of an ambient fluid. This present invention also includes a membrane member which protects the indicator material.

SUMMARY OF THE INVENTION

This invention may be briefly summarized as an on demand usable life indicator comprising: a base member, an indicator material, an adhesive layer, and co-layered cover member. The base member is impermeable to a selected ambient fluid. The indicator material is applied to one side of the base member in a predetermined pattern. The indicator material has a selected composition for providing a visual indication when exposed to a predetermined component of an ambient fluid for a predetermined period of time. The adhesive layer is applied with a predetermined pattern over the exposed side of the indicator material. The adhesive layer has impermeable properties with respect to said ambient fluid. The predetermined pattern being configured for providing exposure of at least one selected portion of the indicator material to the ambient fluid. The co-layered layered cover member covers the adhesive layer. One of the layers being impermeable to the selected ambient fluid for isolating said indicator material from the ambient fluid. A second layer being permeable to the selected ambient fluid. The second layer is adhered to the adhesive layer for providing a membrane between the ambient fluid and the indicator material. The first layer is selectably removable from said second layer for exposing the selected portion of the indicating layer to the selected ambient fluid.

In addition to the above summary, the following disclosure is intended to be detailed to insure adequacy and aid in the understanding of the invention. However, this disclosure, showing particular embodiments of the invention, is not intended to describe each new inventive concept which may arise. These specific embodiments have been chosen to show at least one preferred or best mode for the on demand useful life indicator of the present invention. These specific embodiments, as shown in the accompanying drawings, may also include diagrammatic symbols for the purpose of illustration and understanding.

Figure 1:
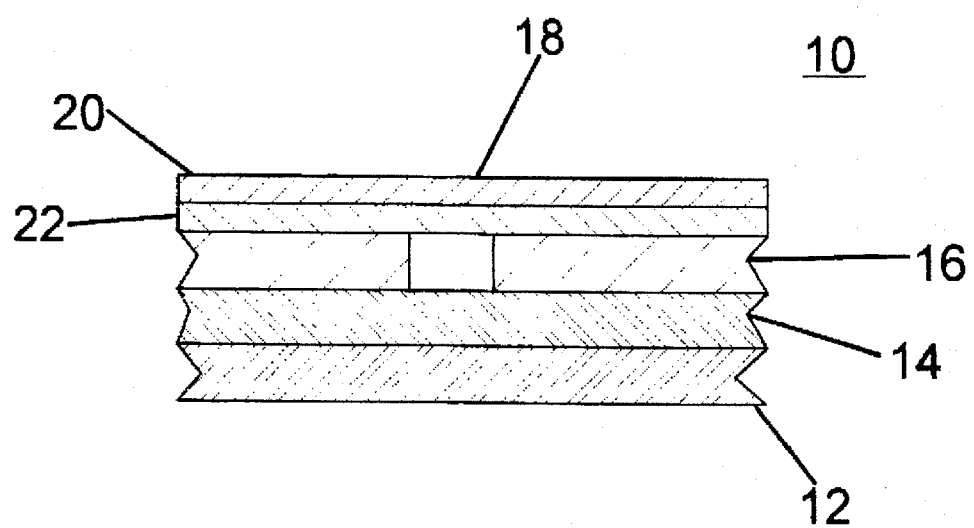
FIG. 1 represents a cross-sectional view of an on demand useful life indicator of the present invention.

In the following description and in the appended claims, various details are identified by specific names for convenience. These names are intended to be generic in their application while differentiating between the various details. The corresponding reference numbers refer to like members throughout the several figures of the drawing.

The drawing accompanying and forming a part of this specification disclose details of construction for the sole purpose of explanation. It is to be understood that structural details may be modified without departing from the concept and principles of the claimed invention. This invention may be incorporated into other structural forms than those that are shown.

DETAILED DESCRIPTION OF THE INVENTION

Referring to the drawing a usable life indicator is generally identified as 10. That usable life indicator 10 includes a base member 12, an indicator material layer 14; an adhesive layer 16; and a co-layered cover member 18.

The base member 12 is preferably made of a material that is impermeable to a selected ambient fluid. The ambient fluid may be either a gas or a liquid. However the base member 12 may be made of a material that is impervious to gas and liquid. This base member 12 may be a flexible thermoplastic material or a metallic foil that is applied as a self-adhesive label.

The indicator material layer 14 is applied onto one side of the base material. Printing the indicator material 14 in a selected pattern is among the methods of application. The indicator material should have a selected composition. This selected composition will provide a visual indication when exposed to a selected component of an ambient fluid for a selected period of time. This indication may be a change of color or a change from a visual color to a lack of color. It may be necessary to apply this indicator material in a controlled or inert atmosphere such as Nitrogen. The selected component should be absent from the controlled atmosphere for avoiding a false indication. It may be necessary to cure or dry the indicator layer to a preferred state.

After the indicator material layer 14 is brought to a preferred cured condition, the adhesive layer 16 is applied thereon and thereover. The adhesive layer may be applied in a selected pattern by a processes such as printing; coating; or laminating. Preferably, the adhesive layer is composed of a material that is impermeable to the selected component of the ambient fluid. Any voids in the adhesive layer will allow the selected component in the ambient fluid to come in contact with the indicator layer. This adhesive layer may be pressure sensitive; heat activated; or contact type.

A co-layered cover member 18 is applied over the adhesive layer 16. This co-layered cover member 18 includes at least two layers. The first or outer layer 20 is impermeable to the selected component of the ambient fluid. The surface of the second or inner layer 22, directly contacting the adhesive layer, is rendered impermeable to the selected component of the ambient fluid due to the impermeability of the adhesive 16. The inner layer 22 has a greater adhesion to the adhesive layer 16 than to the outer layer 20. This allows the outer layer to be selectively removed without removal of the inner layer 22. Removal of the outer layer 20 allows a selected component of the ambient fluid to permeate through inner layer 22 and any voids in the adhesive layer 16. The rate of change of the visual indication of the indicator material layer 14 may be controlled by its composition or by controlling the permeability of the inner layer 22. The inner layer 22 also acts as a membrane for protecting the surface of the adhesive layer 16 and the indicator material layer 14 from abrasion. One Example of co-layered material is Technimagic™ which is produced by Technicote.

The usable life indicator 10 has a relatively long shelf life when the outer layer and the base member are not punctured. It is only when the outer layer 20 is removed that the timing of the period for a selected useful life begins.

The composition of the adhesive layer 16 may be formulated to include the selected component of the ambient fluid. This type of formulation would provide a perceptible change to the indicator material 14 directly in contact with the adhesive layer 16. This arrangement would provide a self-contained norm for judging the degree of color or lack of color. "This self-contained norm may be utilized by visually comparing the area of any indicating material 14 interior of the void areas in the adhesive layer 16 with the self-contained norm. Any visual comparison is made by viewing any visual changes to the indicating material 14 though the exposed surface of inner layer 22 after the outer layer 20 has been removed."

One example of a useable life indicator includes an indicator material layer 14 that is sensitive to an acid or a base component of the ambient fluid. The indicator material 14 may be formulated with litmus like properties. Some examples of materials having litmus properties are Phenolphthalein, Phenolsulfonethalein and the like.

A second example of a useable life indicator includes an indicator material layer 14 that is sensitive to carbon dioxide as the active component of the ambient fluid. The indicator material 14 may be formulated with Oxidation/Reduction properties. One example of those materials that change properties when exposed to carbon dioxide is Thymolphthalein, but not limited thereto.

A third example of a useable life indicator includes an indicator material layer 14 that is sensitive to oxygen as the active component of the ambient fluid. The indicator material 14 may be formulated with Oxidation/Reduction properties. One example of those materials that change properties when exposed to oxygen is Methyl Orange, but not limited thereto.

A fourth example of a useable life indicator includes an indicator material layer 14 that is sensitive to ozone as the active component of the ambient fluid. The indicator material 14 may be formulated with Oxidation/Reduction properties. One example of those materials that change properties when exposed to ozone is Crystal Violet, but not limited thereto.

A fifth example of a useable life indicator includes an indicator material layer 14 that is sensitive to chlorine as the active component of the ambient fluid. The indicator material 14 may be formulated with Oxidation/Reduction properties. One example of those materials that change properties when exposed to chlorine is Metacresol Purple, but not limited thereto.

A sixth example of a useable life indicator includes an indicator material layer 14 that is sensitive to carbon monoxide as the active component of the ambient fluid. The indicator material 14 may be formulated with Oxidation/Reduction properties. One example of those materials that change properties when exposed to carbon monoxide is Alizarin Yellow, but not limited thereto.

As mentioned above, the adhesive layer in any or all of the examples mentioned above may be formulated with the component of the ambient fluid to provide the norm as described above. The color or visual indication of that area of the indicator material 14 not in contact with the adhesive would remain as applied until the outer layer 20 is removed. The area of the indicator material 14 in direct contact with the adhesive layer 16 would change to the color or visual indication that is to be used as a norm.

Directional terms such as "upper", "lower", "inner", "outer" and the like may have been used in the description. These terms are applicable to the embodiments shown and described in conjunction with the drawings. These terms are merely used for the purpose of description in connection with the drawings and do not necessarily apply to the position in which the present invention may be used.

While these particular embodiments of the present invention have been shown and described, it is to be understood that the invention is rot limited thereto and protection is sought to the broadest extent that the prior art allows.

What is claimed is:

1. A useful life indicator comprising:
   a) a base member that is impermeable to a selected ambient fluid;
   b) an indicator material having a first side and an opposite second side, said first side being applied to one side of the base member in a predetermined pattern, said indicator material having a selected composition providing a visual indication when exposed to a predetermined active component of the ambient fluid;
   c) an adhesive applied with a predetermined pattern on a same side of the useful life indicator as the indicator material, said predetermined pattern of adhesive being applied to at least portions of the second side of the indicator material, said adhesive being impereable with respect to the active component of said ambient fluid; said predetermined pattern of the adhesive providing at least one void area that is absent adhesive therein said void area providing exposure of at least one selected portion of the indicator material to the active component of the ambient fluid; and
   d) a co-layered cover member that fully covers said adhesive and the indicator material, said cover member having at least two layers, a first layer of the two layers being impermeable to the selected ambient fluid for isolating said indicator material from the ambient fluid, a second layer of the two layers being permeable to the selected ambient fluid, and being positioned between the adhesive and the first layer said second layer having a greater attraction to the adhesive than to the first layer and said greater attraction resulting in said second layer being adhered to the adhesive for providing a membrane between the ambient fluid and the indicator material, the first layer being selectably removable from said second layer for completely exposing said second layer, thus enabling predetermined active component of the ambient fluid to permeate through the exposed second layer thereby equally and only exposing the selected portion of the indicating material interior of the void areas to the selected ambient fluid, to provide said visual indication said visual indication being observable through the exposed surface of the second layer, the visual indication beginning after removal of said first layer and being completed near the end of a predetermined period of time said membrane further providing abrasion protection for the adhesive and the indicator material during the predetermined period of time.

2. An indicator as recited in claim 1 wherein the predetermined active component of the ambient fluid is carbon dioxide.

3. An indicator as recited in claim 1 wherein the selected composition of the indicator material includes litmus properties, and the adhesive further includes a predetermined pH factor for bringing the indicator material in contact with said adhesive layer to a reference state of indication for providing a visual comparison of the indicator material in contact with the adhesive with the indicator material interior of the at least one void area.

4. An indicator as recited in claim 1 wherein said adhesive further includes pressure sensitive properties.

5. An indicator as recited in claim 1 wherein the base member includes an adhesive coating that is placed on a side of the base member that is opposite to the indicator material.

6. An indicator as recited in claim 1 wherein the base member is a flexible thermoplastic material.

7. An indicator as recited in claim 1 wherein the predetermined active component of the ambient fluid is carbon monoxide.

8. An indicator as recited in claim 1 wherein the predetermined active component of the ambient fluid is oxygen.

9. An indicator as recited in claim 1 wherein the predetermined active component of the ambient fluid is chlorine.

10. An indicator as recited in claim 1 wherein the predetermined active component of the ambient fluid is ozone.

* * * * *